United States Patent
Schallenberger et al.

(10) Patent No.: US 10,821,004 B2
(45) Date of Patent: Nov. 3, 2020

(54) EXPANDABLE BONE GRAFTS AND METHODS OF MANUFACTURE THEREOF

(71) Applicants: Mark Schallenberger, Bozeman, MT (US); Helena Lovick, N. Great Falls, MT (US); Todd Meyer, Bozeman, MT (US)

(72) Inventors: Mark Schallenberger, Bozeman, MT (US); Helena Lovick, N. Great Falls, MT (US); Todd Meyer, Bozeman, MT (US)

(73) Assignee: BACTERIN INTERATIONAL, INC., Belgrade, MT (US)

( * ) Notice: Subject to any disclaimer, the term of this patent is extended or adjusted under 35 U.S.C. 154(b) by 357 days.

(21) Appl. No.: 15/199,458

(22) Filed: Jun. 30, 2016

(65) Prior Publication Data

US 2017/0000624 A1    Jan. 5, 2017

Related U.S. Application Data

(60) Provisional application No. 62/186,569, filed on Jun. 30, 2015.

(51) Int. Cl.
| | | |
|---|---|---|
| A61F 2/44 | (2006.01) | |
| A61L 27/36 | (2006.01) | |
| A61L 27/54 | (2006.01) | |
| A61F 2/30 | (2006.01) | |
| A61L 27/56 | (2006.01) | |

(52) U.S. Cl.
CPC ........ *A61F 2/4455* (2013.01); *A61L 27/3608* (2013.01); *A61L 27/54* (2013.01); *A61F 2002/30187* (2013.01); *A61F 2310/00359* (2013.01); *A61L 27/365* (2013.01); *A61L 27/56* (2013.01); *A61L 2300/404* (2013.01)

(58) Field of Classification Search
CPC .............................. A61F 2/44; A61L 27/3608
See application file for complete search history.

(56) References Cited

U.S. PATENT DOCUMENTS

| | | | |
|---|---|---|---|
| 5,314,476 A | 5/1994 | Prewett et al. | |
| 5,507,813 A | 4/1996 | Dowd et al. | |
| 5,513,662 A | 5/1996 | Morse et al. | |
| 6,124,273 A * | 9/2000 | Drohan | A61K 9/0014 514/13.6 |
| 6,395,311 B2 | 5/2002 | Qi | |
| 6,436,138 B1 | 8/2002 | Dowd et al. | |
| 6,541,024 B1 | 4/2003 | Kadiyala et al. | |

(Continued)

FOREIGN PATENT DOCUMENTS

| | | |
|---|---|---|
| WO | WO 2014/110537 | 7/2014 |
| WO | WO 2014/151091 | 9/2014 |

OTHER PUBLICATIONS

Official Action for U.S. Appl. No. 14/639,902, dated Aug. 25, 2016, 9 pages.

(Continued)

*Primary Examiner* — Nicholas W Woodall
(74) *Attorney, Agent, or Firm* — Sheridan Ross P.C.

(57) ABSTRACT

The present invention relates to compressed bone-based products and methods to make the same. The maintained compressed state of the product serves to enhance the product's inherent osteoconductivity.

20 Claims, 3 Drawing Sheets

(56) References Cited

U.S. PATENT DOCUMENTS

| | | | |
|---|---|---|---|
| 6,620,196 B1* | 9/2003 | Trieu | A61F 2/441 623/17.16 |
| 6,808,585 B2 | 10/2004 | Boyce et al. | |
| 7,312,301 B2* | 12/2007 | Fang | A61L 24/0031 523/122 |
| 7,323,193 B2 | 1/2008 | Morris et al. | |
| 7,582,309 B2 | 9/2009 | Rosenberg et al. | |
| 7,726,002 B2 | 6/2010 | Shimp et al. | |
| 8,133,421 B2 | 3/2012 | Boyce et al. | |
| 8,574,825 B2 | 11/2013 | Shelby et al. | |
| 8,859,007 B2 | 10/2014 | Carter et al. | |
| 8,980,248 B2 | 3/2015 | Shoichet et al. | |
| 9,114,191 B2 | 8/2015 | Shelby et al. | |
| 9,168,138 B2* | 10/2015 | O'Neil | A61F 2/28 |
| 9,675,645 B2* | 6/2017 | Wei | A61K 35/28 |
| 2002/0192263 A1 | 12/2002 | Merboth et al. | |
| 2004/0034434 A1 | 2/2004 | Evans et al. | |
| 2004/0210310 A1* | 10/2004 | Trieu | A61F 2/442 623/17.11 |
| 2004/0249461 A1* | 12/2004 | Ferree | A61F 2/2846 623/17.11 |
| 2004/0258732 A1* | 12/2004 | Shikinami | A61L 27/446 424/426 |
| 2005/0004242 A1* | 1/2005 | Sotome | A61L 27/46 521/61 |
| 2006/0015184 A1* | 1/2006 | Winterbottom | A61F 2/44 623/18.11 |
| 2006/0030948 A1 | 2/2006 | Manrique et al. | |
| 2007/0160622 A1 | 7/2007 | Turnell et al. | |
| 2007/0179607 A1 | 8/2007 | Hodorek et al. | |
| 2008/0091270 A1* | 4/2008 | Miller | A61F 2/4455 623/17.16 |
| 2009/0028957 A1 | 1/2009 | Daniloff | |
| 2010/0036503 A1 | 2/2010 | Chen et al. | |
| 2010/0204699 A1 | 8/2010 | Wei et al. | |
| 2010/0331257 A1* | 12/2010 | Bayon | A61K 38/1875 514/17.2 |
| 2012/0010728 A1 | 1/2012 | Sun et al. | |
| 2013/0136777 A1 | 5/2013 | Behnam et al. | |
| 2013/0190875 A1 | 7/2013 | Shulock et al. | |
| 2013/0345826 A1 | 12/2013 | Li et al. | |
| 2014/0052247 A1* | 2/2014 | Daniel | A61L 27/50 623/13.11 |
| 2014/0142041 A1 | 5/2014 | Koob | |
| 2014/0257516 A1 | 9/2014 | Mills et al. | |
| 2014/0277577 A1 | 9/2014 | Garigapati | |
| 2014/0314822 A1 | 10/2014 | Carter et al. | |
| 2015/0004414 A1 | 1/2015 | Ogura et al. | |
| 2015/0093429 A1 | 4/2015 | Carter et al. | |
| 2015/0251361 A1 | 9/2015 | Meyer et al. | |
| 2016/0287747 A1 | 10/2016 | Schallenberger | |

OTHER PUBLICATIONS

Pietrzak et al., "BMP depletion occurs during prolonged acid demineralization of bone: characterization and implications for graft preparation," Cell and Tissue Banking, 2011, vol. 12(2), pp. 81-88.

Claes et al. "Fracture healing under healthy and inflammatory conditions," Nature Reviews Rheumatology, Mar. 2012, vol. 8, pp. 133-143.

Simmonds et al. "Safety and Effectiveness of Recombinant Human Bone Morphogenetic Protein-2 for Spinal Fusion," Annals of Internal Medicine, Jun. 2013, vol. 158, No. 12, pp. 877-889.

Final Action for U.S. Appl. No. 14/639,902, dated Mar. 28, 2017 10 pages.

Official Action for U.S. Appl. No. 15/397,619, dated Mar. 24, 2017 9 pages Restriction Requirement.

Official Action for U.S. Appl. No. 14/639,902, dated Oct. 5, 2017 10 pages.

Official Action for U.S. Appl. No. 14/639,902, dated Apr. 10, 2018 9 pages.

Official Action for U.S. Appl. No. 15/087,553, dated Jun. 29, 2018 7 pages Restriction Requirement.

Official Action for U.S. Appl. No. 15/397,619, dated Oct. 19, 2017 17 pages.

Notice of Allowance for U.S. Appl. No. 14/639,902, dated Aug. 29, 2018 6 pages.

Notice of Allowability for U.S. Appl. No. 14/639,902, dated Sep. 12, 2018, 3 pages.

U.S. Appl. No. 16/200,408, filed Nov. 26, 2018.

Official Action for U.S. Appl. No. 15/087,553 dated Oct. 31, 2018 13 pages.

Official Action for U.S. Appl. No. 16/200,408, dated Jun. 24, 2020, 10 pages.

\* cited by examiner

EXPANDABLE BONE GRAFTS AND METHODS OF MANUFACTURE THEREOF

CROSS REFERENCE TO RELATED APPLICATIONS

This application claims priority under 35 U.S.C. § 119(e) to U.S. Provisional Patent Application Ser. No. 62/186,569, filed Jun. 30, 2015, which is incorporated herein in its entirety by reference.

FIELD OF THE INVENTION

The invention generally relates to bone-based products retained in a compressed state and methods of manufacture and use thereof. The bone products are specifically designed to present in a compressed state after implantation. The maintained compressed state of the product serves to enhance the product's inherent osteoconductivity.

DESCRIPTION OF THE PRIOR ART

Expandable osteoimplants and methods for manufacturing the same are known in the prior art. The majority of these methods provide a dehydrated product which exhibits expansion in the course of rehydration. Rehydration may take place before, during, or after implantation. The expandable osteoimplants of the prior art exhibit a range of compression states in either the dehydrated state, rehydrated state, or both. U.S. Patent Publication No. 2008/0091270 entitled "Expandable Osteoimplant" to Miller et al., incorporated in its entirety by reference, discloses an osteoimplant comprising an expandable, biocompatible material. The osteoimplant may be used in the compressed state and later rehydrated to expand to an increased size. U.S. Patent Publication No. 2006/0030948 to Manrique et al., incorporated in its entirety by reference, discloses an osteoimplant where demineralized bone particles are mechanically entangled with each other and are then shaped in a mold.

In some instances, the osteoimplants are contained within medical devices or other containment material. U.S. Patent Publication No. 2010/0204699 entitled "Delivery System Cartridge" to Wei et al., incorporated in its entirety by reference, discloses a delivery system comprising a cartridge configured to fit within a cage. The cartridge includes a covering material containing a bone repair substance to transfer the substance to the surroundings upon implantation. U.S. Pat. No. 7,726,002 entitled "Processes for Making Spinal Intervertebral Implant, Interconnections for Such Implant" to Shimp et al., incorporated in its entirety by reference, discloses a cortical bone implant connected with one or more offset pins. U.S. Patent Publication No. 2013/0190875 entitled "Selectively Expanding Spine Cage with Enhanced Bone Graft Infusion" to Shulock et al., incorporated in its entirety by reference, discloses a selectively expanding spine cage. The cage height may be increased to hold and stabilize the vertebrae.

A need remains for bone-based implants which are maintained in an optimal compressed state. By maintaining the compression state, the implants exhibit enhanced osteoconductivity leading to improved bone regeneration, bone fusion, and clinical outcomes. The present invention discloses products and methods that are advantageous over this art as discussed below.

SUMMARY OF THE INVENTION

The disclosed invention is directed to bone-based implants for bone fusion and bone regeneration where the implant is maintained in the desired compressed state upon implantation. The bone-based implants can contain bone fibers, bone particles, bone sponges, or a combination of these bone forms. The bone-based implants are presented to the end user in a compressed state. The bone-based implants can ideally be compressed within a void to provide a contact pressure of about 1 MPa to about 10 MPa. The void can be a containing device such as a spinal cage or a skeletal void within a patient. In some embodiments, the implants can expand upon implantation to exert the contacting pressure in the range of about 1 MPa to about 10 MPa. By exerting the contact pressure, the bone-based implants can provide enhanced osteoconductivity. In some embodiments, the implants can be dehydrated prior to use. The compressed bone-based implants can be contained within a medical device. In some embodiments, the medical device can be a spinal fusion cage. The bone-based implants contained within a medical device can be pre-compressed within the device prior to implantation. The bone-based implants contained within medical devices can expand to the desired compressed state upon implantation.

In some embodiments, the bone materials can be exposed to drying or lyophilization conditions. In some embodiments, the bone materials can be shaped and sized to specific dimensions to enhance entanglement and subsequent final product self-adhesion, flexibility, and compressibility. The bone-based implants can be any suitable shape, including but not limited to, a cube, a block, a strip, or a sphere. The residual moisture content of the product can be less than about 6%. The rehydrated product can be compressible to about 50% to about 5%, to about 30% to about 10% of an original size of the rehydrated product before dehydration. In some embodiments, following compression the rehydrated product can return to its original shape of the product before dehydration. The void to bone ratio of the product can be between about 1:99 and about 1:11.

The bone materials can be cortical bone, cancellous bone, or combinations thereof. In some embodiments, the bone can be fully demineralized, partially demineralized, mineralized or any combinations thereof. The bone can be partially dehydrated, fully dehydrated, or fully hydrated. The bone can be allogeneic, autogeneic, xenogeneic tissues, and combinations thereof. When dehydrated, the bone-based implants can rehydrate in at least one aqueous liquid, and can rehydrate within about 15 seconds to about 20 minutes, 1 minute to about 15 minutes, about 5 minutes to about 10 minutes. The aqueous liquid can be water, saline, buffer, balanced salt solution, blood, bone marrow aspirate, plasma, or combinations thereof.

The bone-based implants can be contained within a medical device apparatus. The medical device apparatuses can be made from biocompatible materials including, but not limited to, bone, ceramics, metals, plastics, biodegradable polymers, and combinations thereof. The medical device apparatus can serve as a mold during the manufacture of the bone-based implants.

An aspect of the invention is a bone-based product adapted to fit within a void. The bone-based product is within the void and exerts an expansion pressure of about 1 MPa to about 10 MPa within the void.

An aspect of the invention is a method of forming a bone-based product compressible to about 20% to about 80% of a pre-dehydrated state. The method includes cutting bone into bone fibers, then entangling the bone fibers in an aqueous solution to produce entangled fibers. The entangled fibers are placed in a mold and dried.

An aspect of the invention is an implantable medical device. The device includes a structure defining a void, and a bone based product. The bone based product is adapted to fit within the void and exert an expansion pressure of about 1 MPa to about 10 MPa within the void.

DETAILED DESCRIPTION OF THE INVENTION

Figure 1:
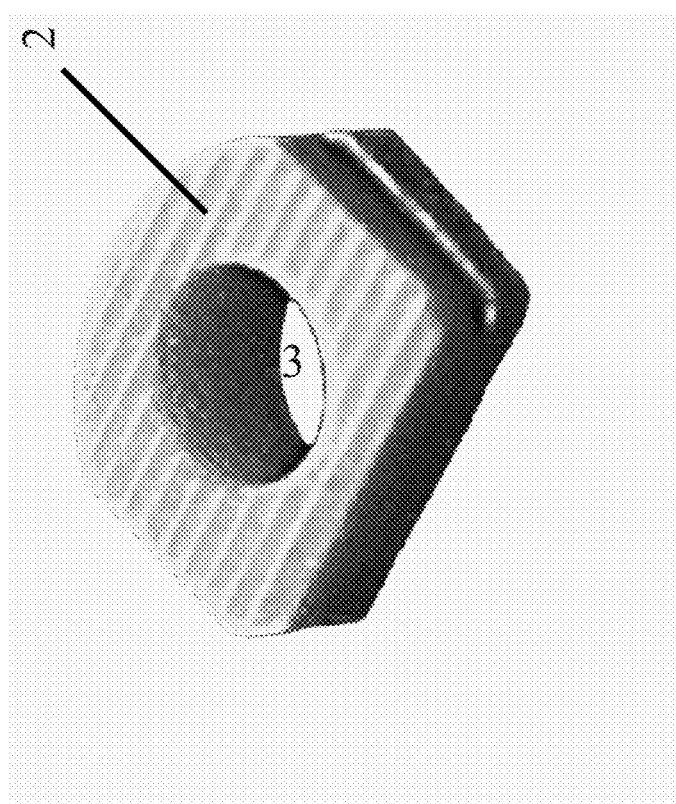
FIG. 1 illustrates a perspective view of a milled cervical spacer.

The present invention relates to bone-based products retained in a compressed state and methods of making the same.

"Allogeneic" or "allograft", as used herein, refers to tissue derived from a non-identical donor of the same species, which can be a DBM.

"Autogeneic" or "autograft", as used herein, refers to tissue derived from and implanted into the same identical patient.

"Biocompatible", as used herein, refers to the property of being biologically compatible with a living being by not causing harm.

"Osteoinductive", as used herein, refers to the ability of a material to induce bone healing via recruitment of osteoprogenitor cells.

"Osteoconductivity", as used herein, refers to the ability of a material to facilitate bone healing by serving as a scaffold for bone regrowth.

"Patient", as used herein, refers to a living recipient of the biomaterial-based implants of the present invention.

"Xenogeneic" or "xenograft", as used herein, is defined as tissue derived from a non-identical donor of a different species.

An aspect of the invention is a bone-based product manufactured to exert a contact pressure of about 1 MPa to about 10 MPa within a void. The void can be a skeletal void within a patient, or a void within an apparatus. The void can be present in a patient due to deterioration of the bone or if the void is created, either due to a break, or intentionally. The patient can be a mammal, including a human, a horse, a cow, a dog, a cat, or the like. The apparatus can be a medical implant, including for example a cage implant, or the like.

The product can be made of bone chips, bone particles, bone fibers, bone chunks, bone sponge, or combinations thereof. A dimension of the bone chips, bone particles, and bone chunks can be about 0.001 mm to about 5 mm, 0.01 mm to about 4 mm, about 0.01 mm to about 3 mm. The bone fibers can be about 0.1 mm to about 30 mm in length and about 0.001 mm to about 10 mm in width. The product can be cut to the dimensions of a void or apparatus, then be fit within the void or apparatus. The product can be stored within the apparatus. The bone of the bone-based product can be cortical bone, or cancellous bone, or combinations thereof. The bone can be fully demineralized bone, a partially demineralized bone and a mineralized bone, or combinations thereof. The bone can be partially dehydrated, fully dehydrated, fully hydrated, or combinations thereof.

After the product is rehydrated, it can expand to about 50% to about 99% of a pre-dehydrated state. The bone-based product can be osteoinductive. The product can be bioconductive.

The products can be provided in a pre-compressed state when the bone-based material of the products is manufactured using the principles described in U.S. patent application Ser. No. 14/639,902, which is incorporated by reference in its entirety, or using the principles described in U.S. Pat. No. 8,574,825, which is incorporated by reference in its entirety. Pre-compressed bone-based implants can be produced by the methods of manufacturing disclosed in U.S. Pat. No. 8,574,825. For example, the bone body can be placed in a processing solution comprising an acid at a pH of greater than about zero to de mineralize the bone body. The bone body can periodically be removed from the first processing solution at specific time intervals to perform a compression test on the bone body, wherein the compression test comprises applying a compressive force in a range from about 10 g-force/cm$^2$ to about 4000 g-force/cm$^2$. After the bone body is uniformly compressed to less than about 60 percent of its original shape, the bone body is exposed to an acid neutralizing processing solution. After the bone body is demineralized and disinfected to the desired level, the bone body can be lyophilized or dried into a compressed state.

The bone-based products can be comprised of a single material or a mixture of materials which can be used as a scaffold during bone regrowth. In some embodiments, the shaped product can be comprised solely of bone tissue.

The bone-based products of the invention have many advantages over the prior art. The hydrated or rehydrated bone-based products of the invention compress under a force of between about 10 g-force/square cm and about 4000 g-force/square cm. The rehydrated or hydrated, bone-based product can be compressible to about 80% of its original size, to about 60% of its original size, to about 20% of its original size, or to about 5% of its original size, without loss of structural integrity or bone cohesion. Upon removal of an external compressing force, the products can substantially return to their original shape. The dehydrated bone-based product can also rehydrate rapidly within an aqueous fluid over a period of about 15 seconds to about 30 minutes, of about 1 minute to about 25 minutes, or of about 5 minutes to about 20 minutes. In some embodiments, the dehydrated bone-based product can also have a high rehydration rate of between about 0.5 mL of liquid/g of product/minute and about 10 mL of liquid/g of product/minute. Suitable aqueous fluids include, but are not limited to, water, saline, buffer, balanced salt solution, blood, bone marrow aspirate, plasma and combinations thereof.

In some embodiments, the product can include a coating. The coating can be an antimicrobial, an antibacterial, or combinations thereof. Suitable antimicrobial coatings include materials such as polycaprolactones, polyethylene glycols, polyhydroxyalkanoates, polyesteramides, polylactides, polyglycolides, poly(lactide-co-glycolide)s, polyorthoesters, polyoxazolines, and polyurethanes, alone or in combination with one another. Suitable antibacterial materials include materials such as antifolates, aminoglycosides, carbapenems, cephalosporins, fluoroquinolines, glycopeptides, macrolides, monobactams, oxazolidones, penicillins, rifamins, sulfonamides and tetracyclines, lone or in combination with one another. In some embodiments, the product can include a coating for viewing the product after implantation using medical imaging, such as x-ray, or other scans. These coatings can include radiopaque materials such as calcium phosphates, hydroxyapatite, bioactive glasses, barium-doped minerals, and other heavy element impregnated minerals (e.g., tantalum, bismuth).

An aspect of the invention is a method of forming a bone-based product. The void to bone ratio of the product can be between about 1:99 to about 1:11. In some embodiments, the void to bone ratio of the produce can be about 1:99, about 1:80, about 1:70, about 1:60, about 1:50, about 1:40, about 1:30, 1:20, about 1:11. The product can be compressed to about 20% to about 80% of a pre-dehydrated state. The method includes cutting bone into bone fibers, then entangling the bone fibers in an aqueous solution to produce entangled fibers. The entangled fibers are placed into a mold and dried in the mold while warming the mold.

The mold can be a shaping device from which the dried bone-based product can be removed before use or the mold can be a surgical implant for introduction to the patient with the dried bone-based product. In the latter instance, the mold can be the containing device. The implant can be a spinal fusion implant. The bone can be cortical bone, cancellous bone, and combinations thereof. The bone can be demineralized bone, a partially demineralized bone, or a mineralized bone, or combinations thereof.

The containing device and removable components can be placed into a drying chamber in a frozen or thawed state. The removable components can include screens, presses, and other hardware to compress, to shape, and/or to retain the materials within the containing device. The drying step can include blowing gas through the containing device and removable components and/or subjecting the apparatus to reduced pressure, heating, lyophilization (under reduced pressure), or a combination of heating and vacuum. The gas used can include, but is not limited to, nitrogen, helium, argon, and combinations thereof. The drying can be performed under reduced pressure between about 1 nTorr and about 740 Torr, including any sub-range or particular value within these endpoints. The drying step can include air flow into or through the containing device and removable components. In some embodiments, the containing device and removable components can provide user-adjustable pressure to allow variance of the compaction of the resultant article. This user-adjustable pressure of the containing device and removable components can allow for articles of varied "sponginess", flexibility, and compression state. Drying can include heating the material to a temperature between about 30° C. and about 80° C., including any sub-range or particular value within these endpoints. In some embodiments the drying temperature can be about 40° C. Drying can take place over the range of about 1 hour to about 48 hours, including any sub-range or particular value within these endpoints. In some embodiments drying takes place for between about 3 hours and about 30 hours, or about 4 hours and about 25 hours. During the drying step, the vacuum can be increased from an initial pressure of about 100 Torr to about 600 Torr, including any sub-range or particular value within these endpoints, to a pressure of about 100 mTorr to about 30,000 mTorr, including any sub-range or particular value within these endpoints. In some embodiments, the end pressure can be between about 800 mTorr and about 3000 mTorr, or about 1800 mTorr.

Figure 2:
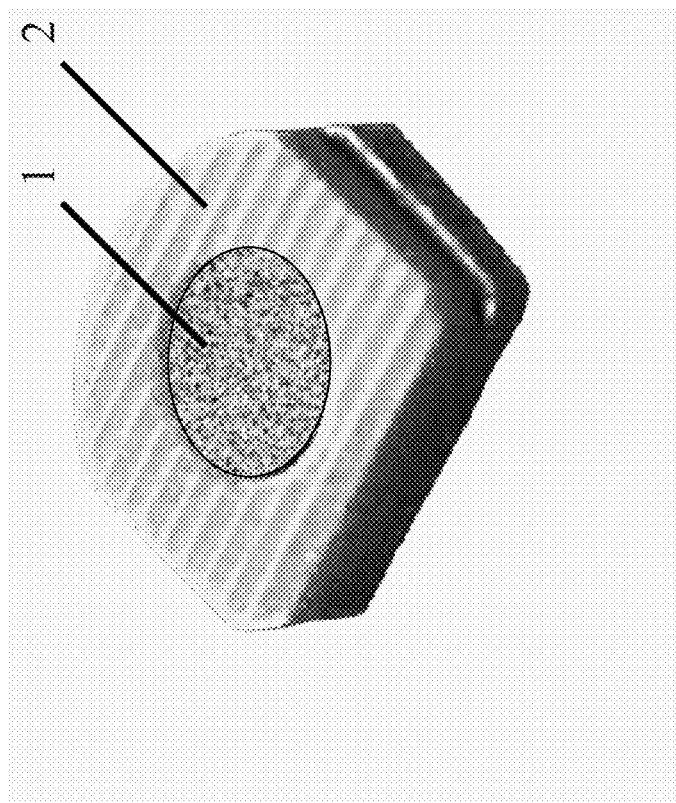
FIG. 2 illustrates a perspective view of a bone-based implant in accordance with the present invention within a milled cervical spacer.

With reference to FIG. 2, following drying, the containing device 2 and removable components can be removed from the drying chamber, and the bone-based product 1 can be removed from the containing device 2 and removable components. In some embodiments, the bone-based product 1 can be retained in the containing device 2. The removable molding components can be removed immediately after drying or at a later date such as immediately prior to implantation.

In some embodiments, following fitting of the bone into the containing device and removable components, the filled components can be frozen at a temperature of about −100° C. to about 0° C., including any sub-range or particular value within these endpoints. In some embodiments, the freezing temperature can be between about −90° C. and about −10° C., or between about −80° C. and about −20° C. The apparatus can be placed into a drying chamber in a frozen or thawed state. Drying can take place over the range of about 1 hour to about 48 hours, including any sub-range or particular value within these endpoints. In some embodiments, the drying time can be between about 3 hours and about 30 hours, or about 4 hours and about 25 hours. In the preferred embodiments, the drying of the bone within the containing device and removable components under the conditions described results in a bone-based article with retained osteoinductivity and a residual moisture content of less than about 6%, less than about 4%, or less than about 2%.

The products formed by the methods of the invention display the highly desired properties of shape retention, cohesiveness, pliability, and compression state upon rehydration for time periods of about 10 minutes to about 1 year, of about 1 hour to about 6 months, of about 3 hours to about 1 month. Suitable aqueous liquids for rehydration include, but are not limited to, water, salines, buffers, balanced salt solutions, blood, and bone marrow aspirate. While not wanting to be bound by theory, it is believed that during the drying process, the fibers are entangled and compressed. The resulting entanglement is maintained over a long duration of time even following rehydration.

The partial expansion of the product can be between about 1% and about 99%, about 10% and about 90%, about 20% and about 80%, about 40% and about 70% of the hydrated initial, non-compressed state of the product. Once the product is inserted into the void, the expansion force of the bone against the containing device or interbody space can range from about 0.1 MPa to about 20 MPa, including any sub-range or particular value within these endpoints. In some embodiments, the compression force can be between about 1 MPa to about 10 MPa, or about 2 MPa to about 8 MPa.

An aspect of the invention is a method to use the bone-based product. The method can include inserting the product into a void in a dehydrated state. After the product is positioned, the product can be rehydrated. In some embodiments, the product can be rehydrated, compressed, then inserted into a void in a hydrated state.

The product can be made of bone chips, bone particles, bone fibers, bone chunks, bone sponge, or combinations thereof. A dimension of the bone chips, bone particles, and bone chunks can be about 0.001 mm to about 5 mm, 0.01 mm to about 4 mm, about 0.01 mm to about 3 mm. The bone fibers can be about 0.1 mm to about 30 mm in length and about 0.001 mm to about 10 mm in width. The product can be cut to the dimensions of a void or apparatus, then be fit within the void or apparatus. The product can be stored within the apparatus or implant. The implant can be a spinal fusion implant. The bone of the bone-based product can be cortical bone, or cancellous bone, or combinations thereof. The bone can be fully demineralized bone, a partially demineralized bone and a mineralized bone, or combinations thereof. The bone can be partially dehydrated, fully dehydrated, fully hydrated, or combinations thereof. After the product is rehydrated, it can expand to about 50% to about 99% of a pre-dehydrated state. In some embodiments, the bone-based article with retained osteoinductivity can have a residual moisture content of less than about 6%, less than about 4%, or less than about 2%.

The products can be provided in a pre-compressed state when the bone-based material of the products is manufactured using the principles described in U.S. patent application Ser. No. 14/639,902, which is incorporated by reference in its entirety, or using the principles described in U.S. Pat. No. 8,574,825, which is incorporated by reference in its entirety. Pre-compressed bone-based implants can be produced by the methods of manufacturing disclosed in U.S. Pat. No. 8,574,825. For example, the bone body can be placed in a processing solution comprising an acid at a pH of greater than about zero to demineralize the bone body. The bone body can periodically be removed from the first processing solution at specific time intervals to perform a compression test on the bone body, wherein the compression test comprises applying a compressive force in a range from about 10 g-force/cm$^2$ to about 4000 g-force/cm$^2$. After the bone body is uniformly compressed to less than about 60 percent of its original shape, the bone body is exposed to an acid neutralizing processing solution. After the bone body is demineralized and disinfected to the desired level, the bone body can be lyophilized or dried into a compressed state.

The bone-based products can be comprised of a single material or a mixture of materials which can be used as a scaffold during bone regrowth. In some embodiments, the shaped product can be comprised solely of bone tissue.

The bone-based products of the invention have many advantages over the prior art. The hydrated or rehydrated bone-based products of the invention compress under a force of between about 10 g-force/square cm and about 4000 g-force/square cm. The rehydrated or hydrated, bone-based product can be compressible to about 80% of its original size, to about 60% of its original size, to about 20% of its original size, or to about 5% of its original size, without loss of structural integrity or bone cohesion. Upon removal of an external compressing force, the products can substantially return to their original shape. The dehydrated bone-based product can also rehydrate rapidly within an aqueous fluid over a period of about 15 seconds to about 30 minutes, of about 1 minute to about 25 minutes, or of about 5 minutes to about 20 minutes. In some embodiments, the dehydrated bone-based product can also have a high rehydration rate of between about 0.5 mL of liquid/g of product/minute and about 10 mL of liquid/g of product/minute. Suitable aqueous fluids include, but are not limited to, water, saline, buffer, balanced salt solution, blood, bone marrow aspirate, plasma and combinations thereof.

The products formed by the methods of the invention display the highly desired properties of shape retention, cohesiveness, pliability, and compression state upon rehydration for time periods of about 10 minutes to about 1 year, of about 1 hour to about 6 months, of about 3 hours to about 1 month. Suitable aqueous liquids for rehydration include, but are not limited to, water, salines, buffers, balanced salt solutions, blood, and bone marrow aspirate. While not wanting to be bound by theory, it is believed that during the drying process, the fibers are entangled and compressed. The resulting entanglement is maintained over a long duration of time even following rehydration.

The partial expansion of the product can be between about 1% and about 99%, about 10% and about 90%, about 20% and about 80%, about 40% and about 70% of the hydrated initial, non-compressed state of the product. Once the product is inserted into the void, the expansion force of the bone against the containing device or interbody space can range from about 0.1 MPa to about 20 MPa, including any sub-range or particular value within these endpoints. In some embodiments, the compression force can be between about 1 MPa to about 10 MPa, or about 2 MPa to about 8 MPa.

FIG. 1 depicts a void 3 within an apparatus 2. In some embodiments, the apparatus can be a void in a patient rather than an apparatus. The void 3 can be intentionally created, or in the event the void is in a patient, the void can be created with a drill, or can be the result of degradation or injury. The void 3 can be any shape or size. In some embodiments, the apparatus 2, can be used as a mold to prepare a bone-based product. In other embodiments, the apparatus 2 can be later implanted into a patient.

FIG. 2 illustrates a perspective view of a bone-based product 1 formed by the method of this invention. The bone-based product 1 can be compressed and held to a specific compression level. The compression can occur during the drying process. Once the drying process is complete the bone-based product 1 can hold a compression level reduced from its hydrated/re-hydrated form. The maintained compression state of the dried bone-based product 1 can be about 99% to about 1%, about 90% to about 10%, about 80% to about 20%, or about 70% to about 40%, of the hydrated initial, non-compressed state of the product.

In some embodiments, the implant can be placed within an apparatus 2, which can be an external implant or cage. FIG. 2 illustrates the containment of the bone-based product 1 within an apparatus 2, which can be a milled cervical spacer. When placed inside a containing device, the containing device can maintain the compressed state of the bone-based product 1. In some embodiments, the containing device can maintain the compressed state of the bone-based product 1 after implantation into a patient. When implanted into a patient, the bone-based product 1 can partially expand. The partial expansion of the product can be between about 1% to about 99%, about 10% to about 90%, about 20% to about 80%, about 40% to about 70% of the hydrated initial, non-compressed state of the product.

The implants can then be placed under compression into a containment device. In some embodiments, the bone-based implants can be formed under pressure using the containment device as a mold as described in U.S. patent application Ser. No. 14/639,902. For example, a method of forming the bone-based products 1 can include placing the demineralized bone body within a containing device. In some embodiments, the containing device can have removable components which can fully enclose the bone fibers or bone body. The containing device and removable components can be perforated to fully or partially to allow removal of moisture from the bone during the drying step. The containing device can be composed of various materials such as, but not limited to, bone, ceramics, elastomers, aluminum, stainless steel, thermoplastics, any other metals, or combinations thereof. The containing device or mold dimensions can be pre-set or adjustable to the desired final bone-based product dimensions. The containing device and removable components can apply adjustable inward pressure.

The bone-based product 1 can be shaped specifically to fill a void. The void can be determined by pre-assessment and measurement of a void, such as a bone void within a patient. Alternatively, the void can be the interior of a medical device such as a spinal cage implant. The final use of the shaped product 1 can be placement within a void of the patient.

The bone-based products can be sized appropriately so that placement within a cavity of specific dimensions generates a defined compression force upon the bone-based implant 1. The defined compression forces upon the bone-based implant 1 are such that the compressed state provides an implant of enhanced osteoconductivity to facilitate graft incorporation and bone fusion progression.

Figure 3:
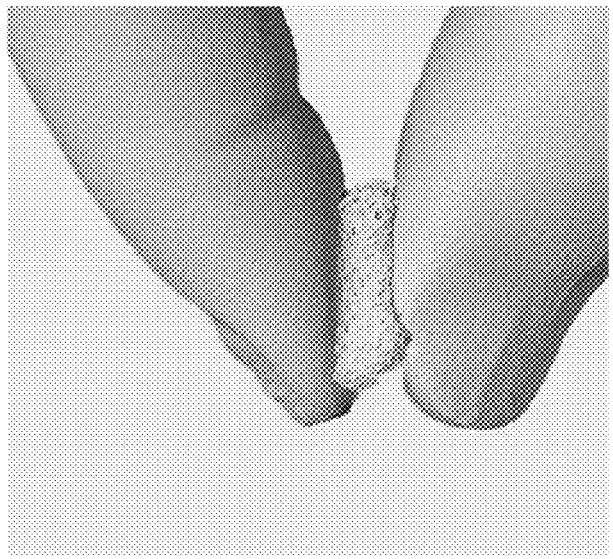
FIG. 3 illustrates a compressible bone-based implant for use in accordance with the present invention.

FIG. 3 depicts the bone body compressed between two fingers. As illustrated in FIG. 3, the bone body remains intact under compression. Furthermore, the bone body is compressed to between about 5% to about 80% of its pre-compressed size. After the compressive force is removed, the bone body returns to between about 50% and about 100% of its original size.

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A bone-based product adapted to fit within a void, wherein when the bone-based product comprises entangled bone fibers, and is within the void, the bone-based product exerts an active expansion pressure on a surface of the void of about 1 MPa a to about 10 MPa, wherein the bone-based product is a body, wherein the bone-based product comprises a void to bone ratio of between about 1:99 and about 1:11, and wherein the bone fibers are entangled such that at least one property of shape retention, cohesive, pliability and compression state are maintained for a period of between about 10 minutes and about 1 year upon rehydration.

2. The bone-based product of claim 1, wherein the void is contained within a medical apparatus.

3. The bone-based product of claim 2, wherein the medical apparatus is a medical implant.

4. The bone-based product of claim 1, wherein the product further comprises a material selected from the group consisting of bone chips, bone particles, bone chunks, bone sponge, and combinations thereof.

5. The bone-based product of claim 1, wherein the bone-based product is produced from cortical bone, cancellous bone and combinations thereof.

6. The bone-based product of claim 1, wherein the bone-based product is produced from at least one of a fully demineralized bone, a partially demineralized bone, a mineralized bone, and combinations thereof.

7. The bone-based product of claim 1, wherein the bone-based product is at least one of a partially dehydrated, a fully dehydrated, or a fully hydrated.

8. The bone-based product of claim 1, wherein the product is dehydrated and when it is rehydrated, expands to about 50% to about 99% of a pre-dehydrated state.

9. The bone-based product of claim 1, wherein the bone-based product is osteoinductive.

10. The bone-based product of claim 1, wherein the bone-based product consists of a bone.

11. The bone-based product of claim 1, wherein a residual moisture content of the bone-based product is less than about 6%.

12. The bone-based product of claim 1, further comprising a coating, wherein the coating is an antibacterial coating, and wherein a material of the antibacterial coating is one of an antifolate, an aminoglycoside, a carbapenem, a cephalosporin, a fluoroquinoline, a glycopeptide, a macrolide, a monobactam, an oxazolidone, a penicillin, a rifamin, a sulfonamide, a tetracycline, or combinations thereof.

13. An implantable medical device, comprising:
a structure comprising a void; and
a bone-based product comprising entangled bone fibers, wherein the bone-based product is adapted to fit within the void, wherein the bone-based product exerts an active expansion pressure on a surface of the void of about 1 MPa to about 10 MPa, wherein a material of the bone-based product consists of a bone, and wherein the bone fibers are entangled such that at least one property of shape retention, cohesive, pliability and compression state are maintained for a period of between about 10 minutes and about 1 year upon rehydration.

14. The implantable medical device of claim 13, wherein the bone is selected from the group consisting of cortical bone, cancellous bone, and combinations thereof.

15. The implantable medical device of claim 13, wherein the structure is a surgical implant.

16. The implantable medical device of claim 13, wherein the bone is fully demineralized bone.

17. The implantable medical device of claim 13, wherein the bone-based product further comprises a material selected from the group consisting of bone chips, bone particles, bone chunks, bone sponge, and combinations thereof.

18. The implantable medical device of claim 13, wherein a material of the structure is at least one of a bone, a ceramic, a metal, a plastic, or a biodegradable polymer.

19. The implantable medical device of claim 13, wherein the bone-based product comprises a void to bone ratio of between about 1:99 and about 1:11.

20. The implantable medical device of claim 13, further comprising a coating, wherein the coating is an antibacterial coating, and wherein a material of the antibacterial coating is one of an antifolate, an aminoglycoside, a carbapenem, a cephalosporin, a fluoroquinoline, a glycopeptide, a macrolide, a monobactam, an oxazolidone, a penicillin, a rifamin, a sulfonamide, a tetracycline, or combinations thereof.

* * * * *